US010577301B2

(12) United States Patent
Keyes et al.

(10) Patent No.: US 10,577,301 B2
(45) Date of Patent: Mar. 3, 2020

(54) USING PRESSURIZED WET GAS LINES TO AVOID FOULING IN PURIFIED TEREPHTHALIC ACID (PTA) FILTERS AND LINES

(71) Applicant: BP Corporation North America Inc., Houston, TX (US)

(72) Inventors: Timothy H. Keyes, Naperville, IL (US); Thomas Bartos, Arden, NC (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/823,988

(22) Filed: Nov. 28, 2017

(65) Prior Publication Data

US 2018/0312460 A1    Nov. 1, 2018

Related U.S. Application Data

(60) Provisional application No. 62/491,808, filed on Apr. 28, 2017.

(51) Int. Cl.
*C07C 51/47* (2006.01)
*C07C 51/43* (2006.01)
(Continued)

(52) U.S. Cl.
CPC .............. *C07C 51/47* (2013.01); *B01D 33/06* (2013.01); *B01D 33/60* (2013.01); *B01D 33/62* (2013.01);
(Continued)

(58) Field of Classification Search
CPC ......... C07C 51/47; C07C 51/42; C07C 51/43; C07C 51/487
(Continued)

(56) References Cited

U.S. PATENT DOCUMENTS 2,741,369 A   4/1956  Fest
5,723,656 A   3/1998  Abrams
(Continued)

FOREIGN PATENT DOCUMENTS

WO   WO 2011/144935       11/2011
WO   WO-2011144935 A1 *   11/2011    ............. C07C 51/43
(Continued)

*Primary Examiner* — Deborah D Carr
(74) *Attorney, Agent, or Firm* — McDonnell Boehnen Hulbert & Berghoff LLP

(57) ABSTRACT

Processes for recovering a purified aromatic carboxylic acid include contacting a crude aromatic carboxylic acid with hydrogen in the presence of a catalyst in a hydrogenation reactor to form a purified aromatic carboxylic acid; crystallizing the purified aromatic carboxylic acid to form a solid/liquid mixture comprising purified aromatic carboxylic acid solids; filtering the solid/liquid mixture in a rotary pressure filter apparatus to remove a liquid filtrate, washing the solid/liquid mixture in the rotary pressure apparatus with a wash fluid to form a washed solid/liquid mixture, and drying the washed solid/liquid mixture in the rotary pressure apparatus with an inert gas to form a filter cake comprising purified aromatic carboxylic acid solids and a wet gas stream; withdrawing the wet gas stream from the rotary pressure filter apparatus while maintaining the wet gas stream at a pressure above ambient; and recovering the purified aromatic carboxylic acid solids from the filter cake.

14 Claims, 2 Drawing Sheets

(51) Int. Cl.
  *C07C 63/26* (2006.01)
  *B01D 33/60* (2006.01)
  *B01D 33/62* (2006.01)
  *B01D 33/06* (2006.01)
  *C07C 51/42* (2006.01)
  *C07C 51/487* (2006.01)
  *B01D 9/00* (2006.01)

(52) U.S. Cl.
  CPC .............. *C07C 51/42* (2013.01); *C07C 51/43* (2013.01); *C07C 51/487* (2013.01); *C07C 63/26* (2013.01); *B01D 2009/0086* (2013.01)

(58) Field of Classification Search
  USPC ........................................................ 562/485
  See application file for complete search history.

(56) References Cited

U.S. PATENT DOCUMENTS

| | | |
|---|---|---|
| 6,137,001 A | 10/2000 | Broeker et al. |
| 7,807,060 B2 | 10/2010 | Schmid |
| 7,935,844 B2 | 5/2011 | Bartos |
| 7,935,845 B2 | 5/2011 | Bartos |
| 8,173,834 B2 | 5/2012 | Bartos |
| 9,486,722 B2 | 11/2016 | Keyes et al. |
| 2005/0051473 A1 | 3/2005 | Suss et al. |

FOREIGN PATENT DOCUMENTS

| | | | | |
|---|---|---|---|---|
| WO | WO 2012/001389 | 1/2012 | | |
| WO | WO-2012001389 A1 * | 1/2012 | .............. | C07C 51/43 |
| WO | WO 2012/038751 | 3/2012 | | |
| WO | WO-2012038751 A2 * | 3/2012 | .............. | B01D 9/00 |
| WO | WO 2016/014830 | 1/2016 | | |

* cited by examiner

USING PRESSURIZED WET GAS LINES TO AVOID FOULING IN PURIFIED TEREPHTHALIC ACID (PTA) FILTERS AND LINES

TECHNICAL FIELD

The present teachings relate generally to processes for manufacturing aromatic carboxylic acids, and in particular, to processes for purifying crude aromatic carboxylic acids.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution using a noble metal catalyst. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

In conventional processes, after hydrogenation, a rotary pressure filter apparatus is used to separate the purified carboxylic acid solids from a solid/liquid mixture. A two-phase wet gas stream exits the rotary pressure filter apparatus through a wet gas line. The wet gas line leads to a separation zone. The pressure in the wet gas line drops when the wet gas stream exits the rotary pressure filter apparatus, causing evaporation of solvent in the wet gas line. Because the wet gas stream is a two-phase gas/liquid stream containing inert gases, flashing is more likely than if it were only a liquid stream. The solids formed after evaporation cause fouling in the filter apparatus and thus require shutting down the system in order to clean the filter apparatus. Heating the inert gas and/or wash fluid entering the filter apparatus also leads to increased evaporation, and thus increased fouling in the filter and the wet gas line.

Thus, there is a need for a process for reducing fouling in the filter apparatus and wet gas line and thus, increase run time of the system.

SUMMARY

The scope of the present invention is defined solely by the appended claims, and is not affected to any degree by the statements within this summary.

According to one aspect of the invention, a process for recovering a purified aromatic carboxylic acid is provided. The process comprises contacting a crude aromatic carboxylic acid with hydrogen in the presence of a catalyst in a hydrogenation reactor to form a purified aromatic carboxylic acid; crystallizing the purified aromatic carboxylic acid to form a solid/liquid mixture comprising purified aromatic carboxylic acid solids; filtering the solid/liquid mixture in a rotary pressure filter apparatus to remove a liquid filtrate, washing the solid/liquid mixture in the rotary pressure apparatus with a wash fluid to form a washed solid/liquid mixture, and drying the washed solid/liquid mixture in the rotary pressure apparatus with an inert gas to form a filter cake comprising purified aromatic carboxylic acid solids and a wet gas stream; withdrawing the wet gas stream from the rotary pressure filter apparatus while maintaining the wet gas stream at a pressure above ambient; and recovering the purified aromatic carboxylic acid solids from the filter cake.

According to another aspect of the invention, a system for recovering a purified aromatic carboxylic acid is provided. The system comprises a hydrogenation reactor configured for contacting a crude aromatic carboxylic acid with hydrogen in the presence of a catalyst to form a purified aromatic carboxylic acid; a crystallization zone configured for crystallizing the purified aromatic carboxylic acid to form a solid/liquid mixture comprising purified aromatic carboxylic acid solids; a rotary pressure filter apparatus having a (i) filtering zone configured for filtering the solid/liquid mixture to form a filter cake comprising the purified aromatic carboxylic acid solids, (ii) washing zone configured to wash to filter cake and to form a wet filter cake, and a (iii) drying zone configured to dry the wet filter cake and form a dry filter cake and a wet gas stream; and a wet gas line in fluid communication with the rotary pressure filter apparatus for removing the wet gas from the rotary pressure filter apparatus, the wet gas line having a pressure control mechanism configured for controlling pressure of the wet gas stream at a pressure above ambient.

Other aspects of the invention will be apparent to those skilled in the art in view of the description that follows.

DETAILED DESCRIPTION

Figure 1:
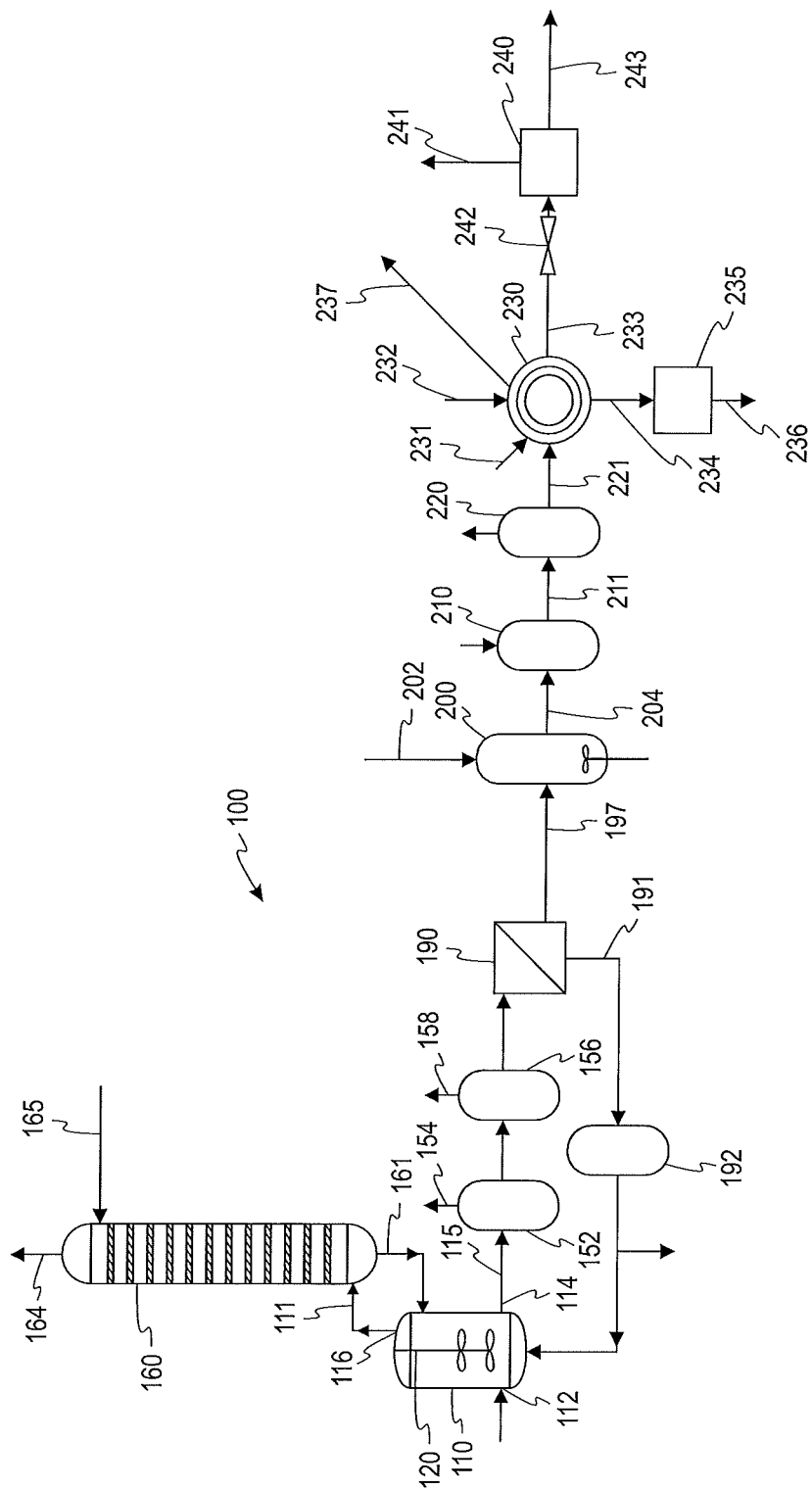
FIG. 1 shows a process flow diagram for manufacturing purified forms of aromatic carboxylic acids in accordance with the present teachings.

By way of general introduction, a process for recovering a purified aromatic carboxylic acid in accordance with the present invention comprises: contacting a crude aromatic carboxylic acid with hydrogen in the presence of a catalyst in a hydrogenation reactor to form a purified aromatic carboxylic acid; crystallizing the purified aromatic carboxylic acid to form a solid/liquid mixture comprising purified carboxylic acid solids; filtering the solid/liquid mixture in a rotary pressure filter apparatus to remove a liquid filtrate; washing the solid/liquid mixture in the rotary pressure filter apparatus with a wash fluid to form a washed solid/liquid mixture; and drying the washed solid/liquid mixture in the rotary pressure filter apparatus with an inert gas to form a filter cake comprising purified aromatic carboxylic acid solids and a wet gas stream. The process further comprises withdrawing the wet gas stream from the rotary pressure filter apparatus while maintaining the wet gas stream at a pressure above ambient and recovering the purified aromatic carboxylic acid solids from the filter cake. The process may further comprise flashing the wet gas stream to form a gas stream and a solid/liquid stream. In some embodiments, the solid/liquid stream is recycled to the hydrogenation reactor.

In some embodiments, the pressure in the wet gas line is controlled with a pressure control mechanism, such as a pressure control valve, located at an entry of a separation zone. In some embodiments, the flashing step is performed in a separation zone at atmospheric pressure.

A system for recovering a purified aromatic carboxylic acid in accordance with the present invention comprises: a hydrogenation reactor configured for contacting a crude aromatic carboxylic acid with hydrogen in the presence of a catalyst to form a purified aromatic carboxylic acid; a crystallization zone configured for crystallizing the purified aromatic carboxylic acid to form a solid/liquid mixture comprising purified aromatic carboxylic acid solids; a rotary pressure filter apparatus having a (i) filtering zone configured for filtering the solid/liquid mixture to form a filter cake comprising the purified aromatic carboxylic acid solids, (ii) washing zone configured to wash to filter cake and to form a wet filter cake, and a (iii) drying zone configured to dry the wet filter cake and form a dry filter cake and a wet gas stream; and a wet gas line in fluid communication with the rotary pressure filter apparatus for removing the wet gas from the rotary pressure filter apparatus, the wet gas line having a pressure control mechanism configured for controlling pressure of the wet gas stream at a pressure above ambient. The system may also comprise a separation zone configured for receiving and flashing the wet gas stream to form a gas stream and a solid/liquid stream, wherein the wet gas line connects the rotary pressure filter apparatus to the separation zone; and a recycling zone configured for directing the solid/liquid stream to the hydrogenation reactor.

Additional features of the above-described processes for manufacturing and recovering purified forms of aromatic carboxylic acid in accordance with the present teachings will now be described in reference to the drawing figures.

FIG. 1 shows a process flow diagram for manufacturing and recovering purified forms of aromatic carboxylic acids in accordance with one embodiment of the present invention. As a brief introduction, the process 100 includes a reaction zone comprising an oxidation reactor 110 configured for liquid phase oxidation of feedstock; a crystallization zone configured for forming crude aromatic carboxylic acid from the liquid phase oxidation reaction mixture, and comprising crystallization vessels 152 and 156; a solid-liquid separation device 190 configured for separating crude aromatic carboxylic acid (and oxidation by-products) from liquid; a mixing zone including a purification reaction mixture make up vessel 200 configured for preparing mixtures of crude aromatic carboxylic acid in purification reaction solvent; a purification zone including a hydrogenation reactor 210 configured for contacting the crude aromatic carboxylic acid with hydrogen in the presence of a catalyst to form a purified aromatic carboxylic acid; and a recovery zone comprising a crystallization zone including vessel 220 configured for forming a slurry stream comprising solid purified aromatic carboxylic acid and a vapor stream, wherein the vapor stream comprises steam and hydrogen; a rotary pressure filter apparatus 230 configured for filtering the solid/liquid mixture to form a filter cake comprising the purified carboxylic acid solids, a wet gas stream, and a liquid filtrate stream; a pressure control mechanism 242, such as a pressure control valve, configured for pressuring maintaining and controlling the pressure of the wet gas stream in a wet gas line; and a separation zone 240 configured for receiving and flashing the pressurized wet gas stream to form a gas stream and a solid/liquid stream.

The integration of processes in FIG. 1 is meant to be purely representative, and various other integrated, and non-integrated configurations may likewise be used.

Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

Representative aromatic feedstock materials suitable for use in the oxidation reactor 110 include but are not limited to aromatic compounds (e.g., hydrocarbons) substituted at one or more positions with at least one group that is oxidizable to a carboxylic acid group. In some embodiments, the positions of the substituents correspond to the positions of the carboxylic acid groups of the aromatic carboxylic acid being prepared. In some embodiments, the oxidizable substituents include alkyl groups (e.g., methyl, ethyl, and/or isopropyl groups). In other embodiments, the oxidizable substituents include oxygen-containing groups, such as a hydroxyalkyl, formyl, aldehyde, and/or keto groups. The substituents may be the same or different. The aromatic portion of feedstock compounds may be a benzene nucleus or it may be bi- or polycyclic (e.g., a naphthalene and/or anthracene nucleus). In some embodiments, the number of oxidizable substituents on the aromatic portion of the feedstock compound is equal to the number of sites available on the aromatic portion. In other embodiments, the number of oxidizable substituents on the aromatic portion of the feedstock is fewer than all such sites (e.g., in some embodiments 1 to 4 and, in some embodiments, 2). Representative feed compounds that may be used in accordance with the present teachings—alone or in combinations—include but are not limited to toluene; ethylbenzene and other alkyl-substituted benzenes; o-xylene; p-xylene; m-xylene; tolualdehydes, toluic acids, alkyl benzyl alcohols, 1-formyl-4-methylbenzene, 1-hydroxymethyl-4-methylbenzene;

methylacetophenone; 1,2,4-trimethylbenzene; 1-formyl-2,4-dimethyl-benzene; 1,2,4,5-tetramethyl-benzene; alkyl-, formyl-, acyl-, and hydroxylmethyl-substituted naphthalenes (e.g., 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene, and the like); and the like; and partially oxidized derivatives of any of the foregoing; and combinations thereof. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Aromatic carboxylic acids manufactured in accordance with the present teachings are not restricted and include but are not limited to mono- and polycarboxylated species having one or more aromatic rings. In some embodiments, the aromatic carboxylic acids are manufactured by reaction of gaseous and liquid reactants in a liquid phase system. In some embodiments, the aromatic carboxylic acid comprises only one aromatic ring. In other embodiments, the aromatic carboxylic acid comprises a plurality (e.g., two or more) aromatic rings that, in some embodiments, are fused (e.g., naphthalene, anthracene, etc.) and, in other embodiments, are not. In some embodiments, the aromatic carboxylic acid comprises only one carboxylic acid (e.g., —$CO_2H$) moiety or a salt thereof (e.g., —$CO_2X$, where X is a cationic species including but not limited to metal cations, ammonium ions, and the like). In other embodiments, the aromatic carboxylic acid comprises a plurality (e.g., two or more) of carboxylic acid moieties or salts thereof. Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, and air may be continuously charged to oxidation reaction vessel 110 through inlets, such as inlet 112. In some embodiments; vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reactor 110, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized acetic acid, water vapor, gaseous by-products from the oxidation reaction, carbon oxides, nitrogen from the air charged to the reaction, unreacted oxygen, and the like, and combinations thereof.

In some embodiments, liquid effluent comprising solid oxidation products slurried in the liquid phase reaction mixture is removed from reaction vessel 110 through slurry outlet 114 and directed in stream 115 to crystallization vessel 152, and in turn crystallization vessel 156, for recovery of a solid product.

The gaseous stream may be removed from the reactor through vent 116 and sent in a stream 111 to a distillation column 160. The distillation column 160 is configured to separate water from the solvent monocarboxylic acid and return a solvent-rich liquid phase to the reactor in line 161. A distilled gaseous stream is removed from the distillation column 160 in line 164 and for further processed. Reflux is returned to the distillation column 160 in line 165. The reflux fluid may include condensed portions of the water rich gas stream 164 or may include fluid from other sources, such as a liquid filtrate stream in stream 237. Examples of further processing of the overhead gas stream and sources of reflux fluids are more fully described in U.S. Pat. Nos. 5,723,656, 6,137,001, 7,935,844, 7,935,845, and 8,173,834.

In some embodiments, solid crude product may be recovered from the liquid by crystallization in one or more stages, such as in a single crystallization vessel or, as shown in FIG. 1, in a series of multiple stirred crystallization vessels. In some embodiments, the crystallization process comprises sequential reductions in temperature and pressure from earlier to later stages to increase product recovery. By way of example, as shown in FIG. 1, crystallization vessels 152 and 156 may be provided in series and in fluid communication, such that product slurry from vessel 152 may be transferred to vessel 156. Cooling in the crystallization vessels may be accomplished by pressure release. One or more of the crystallization vessels may be vented, as at vents 154 and 158, to remove vapor resulting from pressure let down and generation of steam from the flashed vapor to a heat exchange means (not shown).

As shown in FIG. 1, the crystallization vessel 156 is in fluid communication with a solid-liquid separation device 190. The solid-liquid separation device 190 is configured to receive a slurry of solid product from the crystallization vessel 156. In some embodiments, the solid-liquid separation device 190 is further configured to separate a crude solid product and by-products from the liquid. In some embodiments, the separation device 190 is a centrifuge, a rotary vacuum filter, a pressure filter, or the like, or a combination thereof. In some embodiments, the separation device 190 comprises a pressure filter configured for solvent exchange (e.g., by positive displacement under pressure of mother liquor in a filter cake with wash liquid comprising water). Suitable rotary pressure filters are sold by BHS-Sonthofen and are disclosed for example, in U.S. Pat. Nos. 2,741,369, 7,807,060, US Pat. App. 20050051473, US Pat. App. 20150182890, and WO2016014830. The oxidation mother liquor resulting from the separation may exit separation device 190 in stream 191 for transfer to mother liquor drum 192. A portion of the mother liquor and, in some embodiments, a major portion of the mother liquor, may be transferred from drum 192 to oxidation reactor 110. In such a way, monocarboxylic acid solvent, water, catalyst, and/or oxidation reaction by-products dissolved and/or present as fine solid particles in the mother liquor may be returned to the liquid phase oxidation reaction.

As shown in FIG. 1, the stream 197 comprising heated crude solid product may be directed to a mixing zone including a reaction mixture make up vessel 200. The crude solid product in stream 197 may be mixed and slurried in make-up vessel 200 in with a make-up solvent entering vessel 200 through line 202 to form a purification reaction mixture comprising crude aromatic carboxylic acid. The purification reaction mixture prepared in vessel 200 is withdrawn through line 204. In some embodiments, the purification make-up solvent contains water. In some embodiments, the solvent line 202 connects to a holding vessel (not shown) for containing make-up solvent. In other embodiments, the solvent comprises fresh demineralized water fed from a deaerator. In other embodiments, the solvent is supplied from another part of the integrated process 100. For example, in one embodiment, the solvent comprises the condensate obtained from an off-gas separation in column 160 or from vapors recovered from a crystallization zone. In another embodiment, the solvent comprises the solid/liquid stream exiting the separation zone 240. Sources of purification make-up solvent are more fully described, for example, in U.S. Pat. Nos. 5,723,656, 6,137,001, 7,935,844, 7,935,845, and 8,173,834. Suitable sources of purification make-up solvent include demineralized water, steam condensate, condensate from distillation in the oxidation section, such as overhead condensed from stream 334 (discussed below with reference to FIG. 2), and condensate from purification crystallizers such as 220.

Purification reaction mixture exiting vessel 200 through line 204 enters the purification zone. The purification zone includes a purification reactor 210. In some embodiments, the purification reactor 210 is a hydrogenation reactor and purification in the purification reactor 210 comprises contacting the purification reaction mixture comprising crude aromatic carboxylic acid with hydrogen in the presence of a hydrogenation catalyst. In some embodiments, a portion of the purification liquid reaction mixture may be continuously removed from hydrogenation reactor 210 in stream 211 and directed to a crystallization vessel 220 in a downstream crystallization zone. In some embodiments, in crystallization vessel 220, terephthalic acid and reduced levels of impurities may be crystallized from the reaction mixture. The resulting solid/liquid mixture comprising purified carboxylic acid solids formed in vessel 220 may be fed to a rotary pressure filter apparatus 230 in stream 221.

In addition to the solid/liquid mixture in stream 221, a wash fluid and an inert gas are fed to the rotary pressure filter apparatus 230 in streams 231 and 232, respectively. In some embodiments, the inert gas may be commercially available nitrogen. In other embodiments, the inert gas may be a recycled process gas with about 95 percent nitrogen, some oxygen, and other impurities. The inert gas may dry a filter cake in the rotary pressure apparatus 230. In some embodiments, the wash fluid may be a deionized water stream. In other embodiments, the wash fluid may be a recycled water stream with some impurities. The wash fluid may remove impurities from the filter cake.

Figure 2:
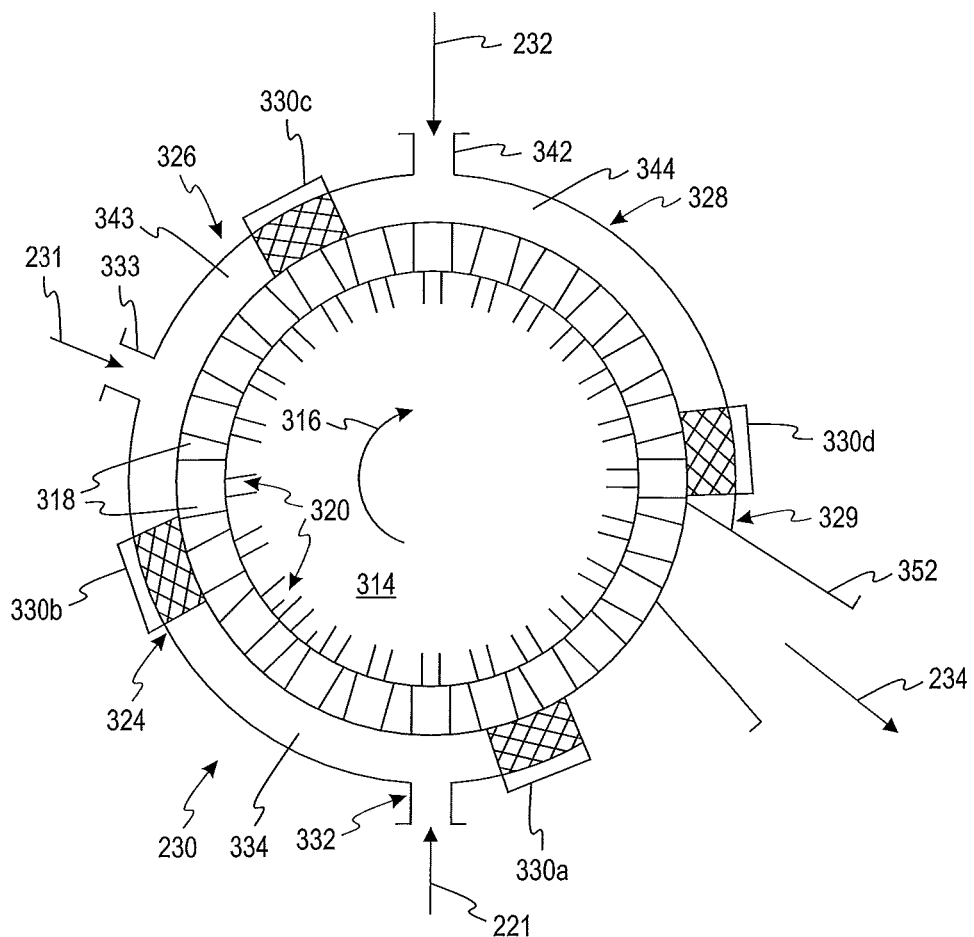
FIG. 2 shows a cross-section of a rotary pressure filter apparatus that is suitable for use in embodiments of the present teachings.

FIG. 2 illustrates one embodiment of a rotary pressure filter apparatus 230. As shown in FIG. 2, the rotary pressure filter apparatus 230 comprises a rotating filter drum 314 which rotates as indicated by arrow 316. A plurality of compartments 318 are arranged around the circumference of the filter drum 314 and rotate with the filter drum 314. The compartments 318 each include a filter member (not shown) adjacent the filter drum. In some embodiments the filter member comprises woven fabric. Each compartment 318 also has associated with it a corresponding outlet pipe 320 which also rotates with the filter drum 314 and the compartments 318. The outlet pipes 320 are configured such that filtrate from each compartment 316 passes through its corresponding filter member adjacent the filter drum 314 and into its corresponding outlet pipe.

The rotary pressure filter apparatus 230 also include a number of stationary components. The rotary pressure filter apparatus 230 may be divided into a plurality of zones, including a filtering zone generally shown at 324, a wash zone generally shown at 326, a drying zone generally at 328 shown a discharge zone generally shown at 329. The filtering zone 324 defines the first stage of a multi-stage process for separating and recovering a solid product from solid-liquid mixtures. Each of the zones are separated from the adjacent zones by sealing members 330a, 330b, 330c, and 330d.

The solid-liquid mixture stream 221 enters the filtering zone 324 of the rotary pressure filter apparatus 230 through inlet 332. The inlet 332 is in fluid communication with plenum 334 which distributes the solid-liquid mixture into compartments 318. As a result of the pressure differential that is maintained between the compartments 318 and the outlet pipes 320 and across the filter member in the compartments, liquid filtrate of the solid-liquid mixture is forced through the filter member in the compartments 318 and into outlet pipes 320. The outlet pipes 320 are in fluid communication with filtrate discharge pipes (shown as stream 237 in FIG. 1) for removing the liquid filtrate from the rotary pressure apparatus 230. The solid components of the solid-liquid mixture remain on the filter member in the form a filter cake.

The compartments 318 now having filter cake continue their rotation into wash zone 326. A wash fluid stream 231 is introduced into the wash zone 326 through inlet 333. The inlet 333 is in fluid communication with plenum 343 which distributes the wash fluid into compartments 318. As a result of the pressure differential that is maintained between the compartments 318 and the outlet pipes 320 and across the filter member in the compartments, the wash fluid is forced into the filter cake that resides on the filter member in the compartments 318 to form a wet filter cake. A portion of the wash fluid is removed through the filter member and into the outlet 320 (as liquid filtrate), taking with it impurities and residual liquids from the solid-liquid mixture that may have adhered to the filter cake or residing in voids of the filter cake. Another portion of the wash fluid remains with the now wet filter cake.

The compartments 318 now having wet filter cake continue their rotation into drying zone 328, where a hot inert drying gas is introduced into the drying zone 328 through inlet 342. The inlet 342 is in fluid communication with plenum 344 which distributes the inert gas into compartments 318. Drying zone 328 may displace the liquid in the wet filter cake down to about 10-12 weight percent forming a dried filter cake and a wet gas stream. The wet gas stream exits the rotary pressure apparatus 230 through outlet pipes 320 in the drying zone 328. The outlet pipes 320 are in fluid communication with a wet gas line 233 (shown in FIG. 1) for removing the wet gas stream from the rotary pressure apparatus 230.

The compartments 318 now having dried filter cake continue their rotation into discharge zone 329. The dried filter cake may be discharged by gravity through discharge outlet 352 as stream 234. In some embodiments, the discharge zone 329 includes a filter cake disengaging device (not shown), such as a blower or scraper to assist with the discharge of the wet filter cake.

Those skilled in the art will appreciate that other configurations of the rotary pressure filter apparatus 230 may be used in accordance with the present invention.

The wet gas stream exits the drying zone 328 of the rotary pressure filter apparatus 230 through outlet pipes 320 and proceeds through wet gas line 233 to separation zone 240. The wet gas stream may be at a temperature of between about 120° C. and about 130° C. exiting the rotary pressure filter apparatus 230. The wet gas stream may comprise inert gases (about 95 percent nitrogen and about 5 percent oxygen), water, acetic acid, and dissolved solids (organic acids). The liquid filtrate stream exits the filtering zone 324 and, in some embodiments, the wash zone 326 of the rotary pressure filter apparatus 230 through outlet pipes 320 to stream 237. The liquid filtrate stream in stream 237 may be returned to the distillation column 160 in line 165. The liquid filtrate stream may comprise water, acetic acid, and dissolved solids (organic acids). The filter cake exits the rotary pressure filter apparatus 230 through stream 234. The filter cake may be dried in a dryer 235, such as a rotary steam tube dryer, to form a purified aromatic carboxylic acid product. The dryer 235 may dry the filter cake until less than about 0.2 weight percent liquid remains in the purified carboxylic acid product. The purified aromatic carboxylic acid product may exit the dryer 235 through stream 236.

In some embodiments, the wet gas stream may be withdrawn from the rotary pressure apparatus 230 while maintaining the wet gas stream at a pressure above ambient pressure. In some embodiments, the pressure of the wet gas line 233 may be controlled such that the pressure of the wet gas stream is at a pressure above 1.5 bar. In some embodiments, the wet gas stream is at a pressure of between about 1.5 bar and about 4 bar. In some embodiments, the wet gas stream is at a pressure of between about 2 bar and about 3 bar. In some embodiments, the wet gas stream is at a pressure of about 2 bar.

The pressure of the wet gas line 233 may be maintained and controlled with a pressure control mechanism 242 located at an entry of the separation zone 240. The separation zone 240 may be configured for receiving and flashing/evaporating the pressurized wet gas stream to form a gas stream and a solid/liquid stream. The separation zone 240 may comprise a knock out drum. The flashing step may be performed at atmospheric pressure.

In some embodiments, the solid/liquid stream may be recycled to the hydrogenation reactor 210 by directing the solid/liquid stream in stream 243 to reaction mixture make up vessel 200, where it may be used as a solvent and then sent to the hydrogenation reactor 210. In some embodiments, the solid/liquid stream in stream 243 may be sent to waste water treatment.

The gas stream may be vented through stream 241 to the atmosphere or directed to a catalytic oxidation unit to remove impurities before being vented to the atmosphere.

By maintaining a wet gas stream pressure above ambient pressure, and in some embodiments between about 1.5 bar and about 4 bar, the wet gas stream does not flash or evaporate in the wet gas line. Thus, the solids in the wet gas line remain in solution and do not cause fouling in the wet gas line or in the rotary pressure filter apparatus 240. Flashing/evaporation occurs in the separation zone 240, which is equipped to handle solids. By avoiding fouling, the system can run continuously without shutting down to clean the filter and/or wet gas line. Heating up the inert gas or the wash fluid, rather than controlling the pressure, still results in evaporation in the wet gas line and thus fouling of the filters and wet gas line.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for recovering a purified aromatic carboxylic acid comprising:
    contacting a crude aromatic carboxylic acid with hydrogen in the presence of a catalyst in a hydrogenation reactor to form a purified aromatic carboxylic acid;
    crystallizing the purified aromatic carboxylic acid to form a solid/liquid mixture comprising purified aromatic carboxylic acid solids;
    filtering the solid/liquid mixture in a filtering zone of a rotary pressure filter apparatus to form a filtered solid-liquid mixture and a liquid filtrate stream;
    withdrawing the liquid filtrate stream from the filtering zone of the rotary pressure filter apparatus;
    washing the filtered solid/liquid mixture in a washing zone of the rotary pressure filter apparatus with a wash fluid to form a washed solid/liquid mixture;
    drying the washed solid/liquid mixture in a drying zone of the rotary pressure filter apparatus with an inert gas to form a filter cake comprising purified aromatic carboxylic acid solids and a wet gas stream;

withdrawing the wet gas stream from the drying zone of the rotary pressure filter apparatus while maintaining the wet gas stream at a pressure above ambient; and recovering the purified aromatic carboxylic acid solids from the filter cake.

2. The process of claim 1, further comprising flashing the wet gas stream to form a gas stream and a solid/liquid stream.

3. The process of claim 2, further comprising recycling the solid/liquid stream to the hydrogenation reactor.

4. The process of claim 1, wherein the wet gas stream is at a pressure above 1.5 bar.

5. The process of claim 1, wherein the wet gas stream is at a pressure of between 2 bar and 3 bar.

6. The process of claim 1, wherein the wet gas stream is at a pressure between 1.5 bar and 4 bar.

7. The process of claim 1, wherein the pressure in the wet gas line is controlled with a pressure control mechanism located at an entry of a separation zone.

8. The process of claim 2, wherein the flashing step is performed in a separation zone at atmospheric pressure.

9. The process of claim 1, wherein the wash fluid removes impurities from the filter cake.

10. The process of claim 1, further comprising oxidizing a substituted aromatic compound in a reaction zone to form the crude aromatic carboxylic acid.

11. The process of claim 1, further comprising drying the filter cake in a dryer to form a purified aromatic carboxylic acid product.

12. The process of claim 1, wherein the aromatic carboxylic acid comprises terephthalic acid.

13. The process of claim 1, further comprising, after washing the filtered solid/liquid mixture, withdrawing at least a portion of the wash fluid from the washing zone of the rotary pressure filter apparatus.

14. The process of claim 1, further comprising separating the wet gas stream to form a gas stream and a solid/liquid stream.

* * * * *